United States Patent [19]

Nassar et al.

[11] Patent Number: 5,401,842
[45] Date of Patent: Mar. 28, 1995

[54] INJECTABLE COMPOSITIONS OF A CEPHALOSPORIN DIHYDRATE SALT

[75] Inventors: Munir N. Nassar, Manlius; Murray A. Kaplan, Syracuse, both of N.Y.

[73] Assignee: Bristol-Meyers Squibb Company, New York, N.Y.

[21] Appl. No.: 198,688

[22] Filed: Feb. 18, 1994

Related U.S. Application Data

[63] Continuation of Ser. No. 72,350, Jun. 4, 1993, abandoned, which is a continuation of Ser. No. 941,584, Sep. 8, 1992, abandoned.

[51] Int. Cl.$^6$ .................. C07D 501/46; A61K 31/545
[52] U.S. Cl. ..................................... 540/222; 514/202
[58] Field of Search ........................ 540/222; 514/202

[56] References Cited

U.S. PATENT DOCUMENTS

| | | | |
|---|---|---|---|
| 4,406,899 | 9/1983 | Aburaki et al. | 424/246 |
| 4,910,301 | 3/1990 | Kaplan et al. | 540/222 |
| 4,994,451 | 2/1991 | Kaplan et al. | 514/202 |

*Primary Examiner*—Nicholas Rizzo
*Attorney, Agent, or Firm*—Aldo A. Algieri

[57] ABSTRACT

The present invention provides physical admixtures of a new crystalline dihydrochloride dihydrate salt of the cephalosporin antibiotic, cefepime with a pharmaceutically acceptable non-toxic organic or inorganic base. In particular, this invention provides physical admixtures having a temperature and moisture stable crystalline dihydrochloride dihydrate form of cefepime having a specific X-ray powder diffraction pattern as described herein.

3 Claims, 4 Drawing Sheets

INJECTABLE COMPOSITIONS OF A CEPHALOSPORIN DIHYDRATE SALT

CROSS-REFERENCE TO RELATED APPLICATIONS

This is a continuation of application U.S. Ser. No. 08/072,350, filed Jun. 4, 1993, now abandoned which is a continuation of U.S. Ser. No. 07/941,584, filed Sep. 8, 1992, now abandoned.

BACKGROUND OF THE INVENTION

1. Field of the Invention

The present invention relates to admixtures of a temperature and moisture stable crystalline dihydrate form of the cephalosporin antibiotic, cefepime dihydrochloride with a pharmaceutically acceptable non-toxic base.

2. Background Art

The antibiotic cefepime is disclosed by Aburaki, et al., in U.S. Pat. No. 4,406,899, issued Sep. 27, 1983 and has the chemical name of 7-[α-(2-aminothiazol-4-yl)-α-(Z)-methoxyiminoacetamido]-3-[(1-methyl-1-pyrrolidinio)methyl]-3-cephem-4-carboxylate. The cefepime described therein is in the zwitterionic form which is unstable at room temperature and loses 30% or more of its activity on storage at elevated temperatures (e.g. 45° C. and above) for even one week.

In U.S. Pat. No. 4,910,301, issued Mar. 20, 1990 to Kaplan, et al, there is described the preparation of a series of crystalline acid addition salts of cefepime. The sulfuric, di-nitric, monohydrochloric, dihydrochloric, and di- and sesquiorthophosphoric acid addition salts, or solvates thereof, are described and reported to have superior temperature stability compared to the zwitterionic form of the aforementioned Aburaki, et al. Furthermore, the preferred dihydrochloride salt of cefepime is reported to exist in a monohydrate or a dihydrate pseudopolymorphic form. Unfortunately, the dihydrochloride monohydrate salt of cefepime is readily converted to a dihydrate form in the presence of high humidity and the resulting dihydrochloride dihydrate salt of cefepime was found to lose one mole of water when dried in vacuo or over a desiccant. Surprisingly, a new distinct polymorphic crystalline dihydrochloride dihydrate of cefepime has been found and this new dihydrate is both temperature and moisture stable.

In U.S. Pat. No. 4,994,451, issued Feb. 19, 1991 to Kaplan, et al, there is claimed physical admixtures of the crystalline cefepime acid addition salts claimed in Kaplan, et al, U.S. Pat. No. 4,910,301 with pharmaceutically acceptable non-toxic organic or inorganic bases.

SUMMARY OF THE INVENTION

The present invention provides physical admixtures of a new crystalline dihydrochloride dihydrate salt of the cephalosporin antibiotic, cefepime with a pharmaceutically acceptable non-toxic organic or inorganic base. In particular, this invention provides admixtures having a temperature and moisture stable crystalline dihydrochloride dihydrate form of cefepime having a specific X-ray powder diffraction pattern as described herein with L(+) arginine in proportions to provide a pH of about 3.5 to about 7 on dilution of the admixture with water in injectable concentration.

DETAILED DESCRIPTION OF THE INVENTION

The present invention provides vacuum-dried physical admixtures of a pharmaceutically acceptable non-toxic organic or inorganic base with a crystalline dihydrate form of cefepime dihydrochloride which is more stable to temperature and moisture environments than the dihydrate form of cefepime described by Kaplan, et al, in U.S. Pat. No. 4,910,301, and is represented by the following formula The crystalline form of the present stable dihydrate appears as fragile long hair-like crystalline needles or thin rods, which readily fractured into "micro" particles. This new dihydrate is a highly stable hydrate which does not add or lose water under conditions of high or low humidity. The crystal morphology of the present dihydrate is not altered under extreme conditions, for example, under vacuum with $P_2O_5$ at 50° C. for 48 hours, oven drying at 70° C. for 96 hours and in air at 70° C. for more than two months. The water of hydration stability of the crystalline dihydrate form of the present invention is markedly different in both form and behavior from the labile dihydrochloride dihydrate salt of cefepime previously described by Kaplan, et al, which appear as granular, plate-like and variably sized dense crystalline particles.

It should be understood by those skilled in the art that the terms "stable" dihydrate and "labile" dihydrate as used herein and in the claims are meant to refer only to the stability or lability (lack of stability) of the second molecule of water in the respective crystal morphology of the subject crystalline form. The use of the terms "stable" and "labile" do not refer to chemical stability or lack thereof nor is it meant to imply any lack of chemical stability or degradation of the various cefepime crystalline forms.

The physical properties and behavior of the crystalline stable dihydrate of the present invention were found to be remarkably different from the labile dihydrate of the prior art when examined by various standard methods and techniques. The differential scanning calorimetric (DSC) thermogram of the present stable dihydrate displayed a vaporization endotherm peak at about 140°–160° C., immediately followed by an exotherm peak at about 170° C. representing decomposition. The DSC thermogram of the labile cefepime dihydrochloride dihydrate of Kaplan, et al, exhibited a small endotherm at about 75° C. representing loss of the less tightly bound second mole of water.

The thermogravimetric analysis (TGA) thermogram of the present crystalline stable dihydrate confirmed evidence of vapor loss. A sample of the stable dihydrate analyzed by TGA gave a weight loss of about 6.9% when heated from about 75°–115° C. which is in good agreement with the 6.25% water content as determined by Karl Fischer titration. The single weight loss transition for the stable dihydrate contrasts with the 2-stage weight loss previously observed and described for the "labile" dihydrate of Kaplan, et al.

Figure 1:
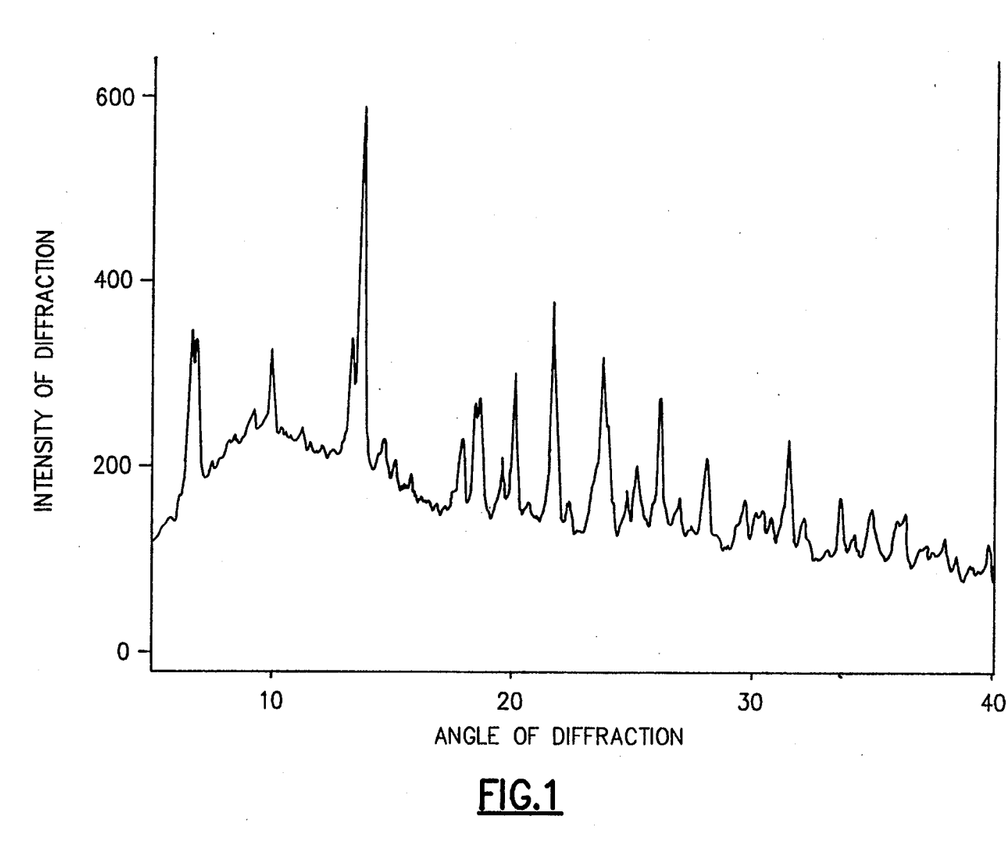
FIG. 1 shows the X-ray powder diffraction pattern of the temperature and moisture stable cefepime dihydrochloride dihydrate.

The new temperature and moisture stable crystalline dihydrate form of cefepime dihydrochloride according to the present invention is characterized by an X-ray powder diffraction pattern substantially as shown in FIG. 1. The X-ray pattern was collected with a Rigaku Geigerflex X-Ray Diffractometer using a nickel filtered copper ($K_\alpha$) average radiation wavelength of 1.5425 Å and a scan range of 5.0 to 40.0 degrees two theta and the significant lines in the drawing of FIG. 1 are listed below in Table 1 wherein "d" refers to interplanar spacings and "$I/I_o$" refers to relative percent intensities.

TABLE 1

| Stable Cefepime Dihydrochloride Dihydrate | |
|---|---|
| d | $I/I_o$ (%) |
| 13.14 | 15 |
| 12.78 | 13 |
| 8.82 | 24 |
| 6.62 | 18 |
| 6.41 | 100 |
| 4.94 | 17 |
| 4.79 | 10 |
| 4.74 | 12 |
| 4.52 | 13 |
| 4.41 | 36 |
| 4.1 | 63 |
| 3.75 | 50 |
| 3.6 | 11 |
| 3.53 | 16 |
| 3.41 | 36 |
| 3.31 | 9 |
| 3.19 | 22 |
| 2.84 | 30 |
| 2.67 | 16 |
| 2.62 | 6 |
| 2.57 | 14 |
| 2.5 | 4 |
| 2.48 | 9 |
| 2.27 | 15 |

Figure 2:
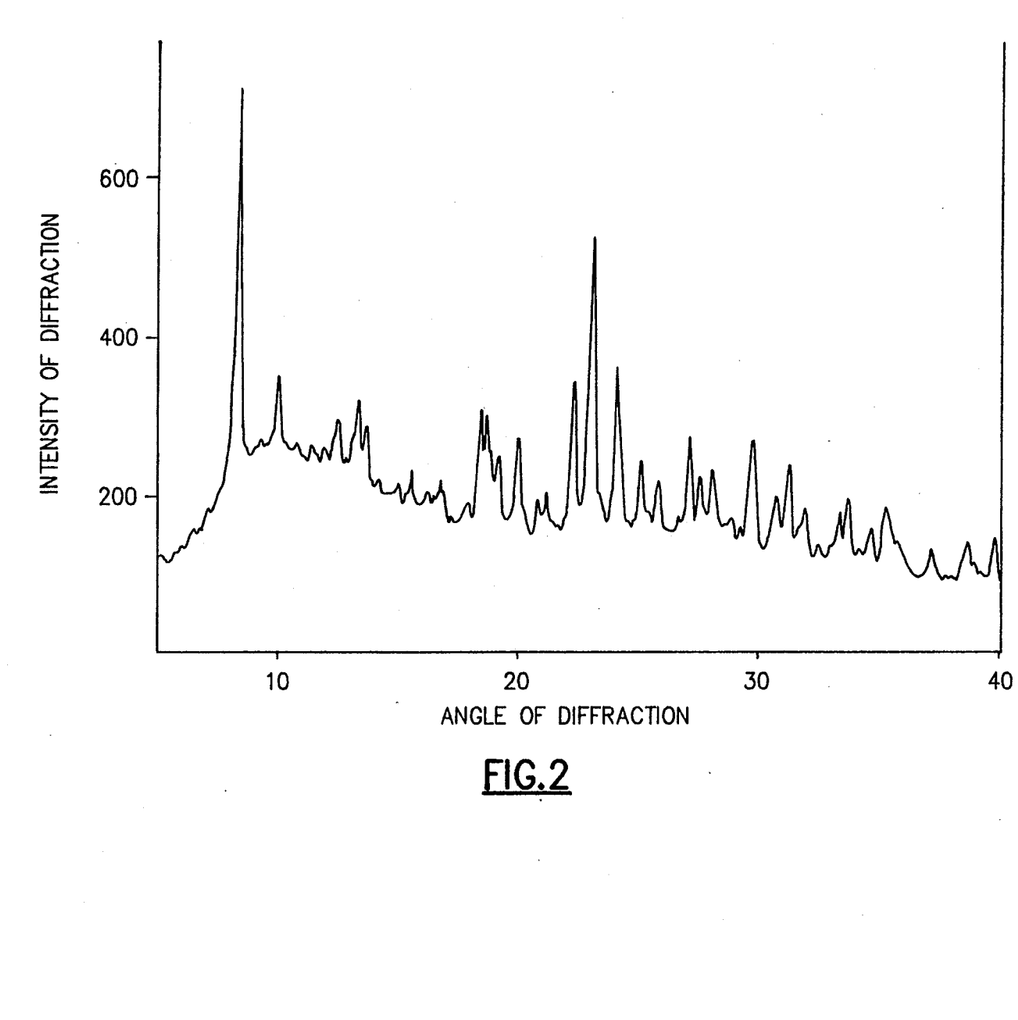
FIG. 2 shows the X-ray powder diffraction pattern of the moisture labile cefepime dihydrochloride dihydrate.

In contrast, the labile dihydrate form of cefepime dihydrochloride as described in U.S. Pat. No. 4,910,301 exhibits an X-ray powder diffraction pattern substantially as shown in FIG. 2. The significant lines in the drawing of FIG. 2 are listed below in Table 2. The differences in the X-ray diffraction for the stable dihydrate of the present invention and the labile dihydrate of the prior art indicate that these two forms are polymorphic.

TABLE 2

| Labile Cefepime Dihydrochloride Dihydrate of U.S. Pat. No. 4,910,301 | |
|---|---|
| d | $I/I_o$ (%) |
| 10.46 | 100 |
| 8.72 | 19 |
| 7.04 | 11 |
| 6.59 | 15 |

TABLE 2-continued

| Labile Cefepime Dihydrochloride Dihydrate of U.S. Pat. No. 4,910,301 | |
|---|---|
| d | $I/I_o$ (%) |
| 6.41 | 9 |
| 5.65 | 8 |
| 4.79 | 14 |
| 4.72 | 12 |
| 4.6 | 11 |
| 4.41 | 23 |
| 3.97 | 34 |
| 3.84 | 71 |
| 3.68 | 38 |
| 3.54 | 15 |
| 3.44 | 12 |
| 3.28 | 23 |
| 3.23 | 11 |
| 3.18 | 13 |
| 3.0 | 27 |
| 2.91 | 10 |
| 2.86 | 18 |
| 2.8 | 11 |
| 2.66 | 12 |
| 2.54 | 11 |
| 2.42 | 7 |
| 2.33 | 10 |
| 2.27 | 17 |

The difference between the new temperature and moisture stable crystalline dihydrate form of cefepime dihydrochloride according to the present invention and the labile dihydrate of the prior art can also be characterized by infrared absorbance spectroscopy. The FT-IR diffuse reflectance spectrum from 4000 cm$^{-1}$ to 600 cm$^{-1}$ was obtained with a Nicolet 20SX spectrometer using a diffuse reflectance accessory. The FT-IR samples were prepared by gently mixing 5.0 mg of sample and 400 mg of KBr in an agate mortar and transferred to a 13 mm sample cup and leveled. The sample cup was placed in the accessory and each sample scanned for 100 times at 4 cm$^{-1}$ resolution and ratioed against a blank KBr sample.

Figure 3:
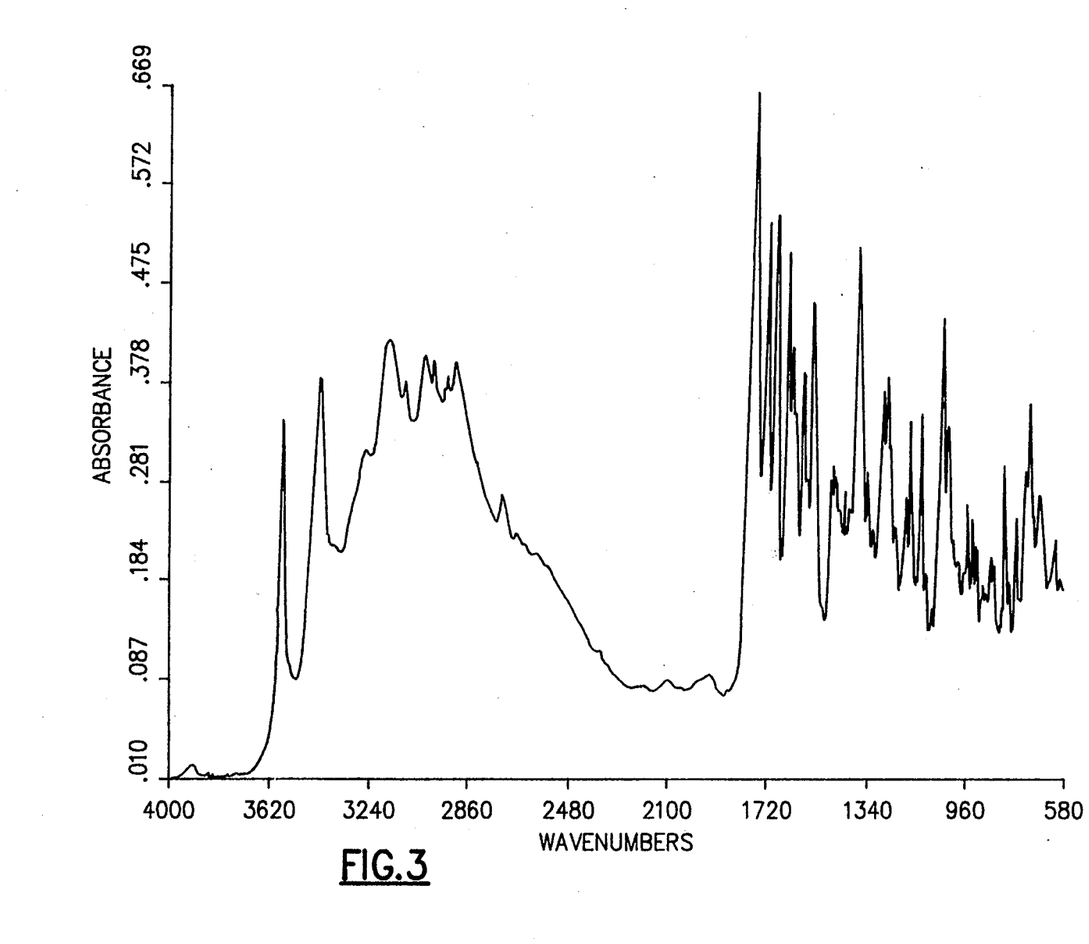
FIG. 3 shows the infrared (FT-IR diffuse reflectance) absorption spectrum of the temperature and moisture stable cefepime dihydrochloride dihydrate.
Figure 4:
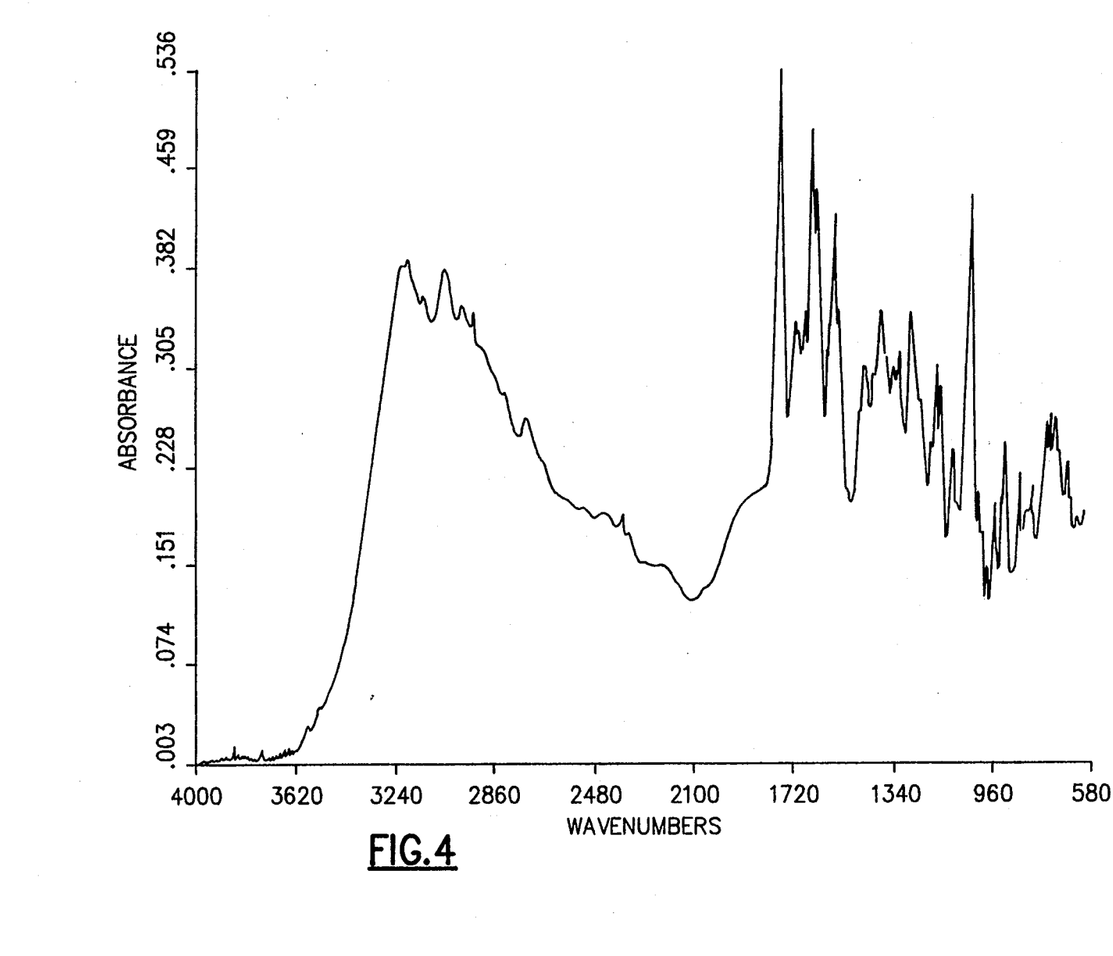
FIG. 4 shows the infrared (FT-IR diffuse reflectance) absorption spectrum of moisture labile cefepime dihydrochloride dihydrate.

The infrared absorbance spectrum of the crystalline dihydrate form of cefepime dihydrochloride according to the present invention is shown in FIG. 3 while the infrared absorbance spectrum of the labile dihydrate of cefepime described by Kaplan, et al, in U.S. Pat. No. 4,910,301 is shown in FIG. 4. As can be seen by a comparison of the spectra, the infrared absorbance of the two dihydrates appear to be substantially different. In particular, the crystalline dihydrate of the present invention exhibits characteristic infrared absorbance peaks at 3574 cm$^{-1}$ and 3432 cm$^{-1}$ as indicated by the FT-IR diffuse reflectance spectrum as shown in FIG. 3.

In addition, the present inventors have discovered that there are major differences in the effect of high and low humidity on moisture uptake, degree and reversibility of hydration and crystalline structure between the cefepime dihydrochloride hydrates of the prior art and the cefepime dihydrochloride dihydrate of the present invention.

In order to observe whether or not moisture had any effect on the various crystalline hydrate forms, each crystalline form was examined under various humidity environments which were prepared using saturated salt solutions in closed glass containers and which were placed in temperature controlled stability stations. The relative humidities (RH) were measured using a Lufft Model HTAB-176 hygrometer calibrated at 42% RH. The following humidity stations were utilized: 87% RH/25° C., $ZnSO_4.7H_2O$; 55% RH/25° C., $Ca(NO_3)_2$;

33% RH/25° C., MgCl$_2$. 6H$_2$O and 80% RH/37° C. (commercial Forma Scientific "Environmental Station").

The hygroscopicity of crystalline cefepime dihydrochloride monohydrate as described by Kaplan, et al, in U.S. Pat. No. 4,910,301 was evaluated by exposing 20 to 30 mg samples of antibiotic substance to 25° C./55% RH, 25° C./87% RH or 37° C./80% RH in open, 10 mL Type I glass vials. At periodic time intervals the vials were removed, stoppered, sealed and tested by Karl Fischer titration (Photovolt Corporation, Aquatest IV Titrator).

TABLE 3

Hygroscopicity of Cefepime Dihydrochloride Monohydrate*

| Time (Days) | Percent Water Content (Karl Fischer) | | |
| --- | --- | --- | --- |
| | 25° C./55% RH | 25° C./87% RH | 37° C./80% RH |
| 0.08 | — | 5.98 | 6.16 |
| 0.17 | — | 6.34 | 6.17 |
| 0.25 | — | 6.10 | 6.08 |
| 0.33 | — | 6.16 | 5.68 |
| 1.0 | — | 6.14 | 5.98 |
| 2.0 | — | 5.73 | 6.22 |
| 3.0 | — | 6.26 | 6.33 |
| 4.0 | — | 6.26 | 6.35 |
| 7.0 | 2.88 | 6.00 | 6.50 |
| 14.0 | 3.32 | 6.71 | 6.69 |
| 21.0 | — | 6.44 | 6.45 |
| 28.0 | — | 7.81 | 6.36 |
| 35.0 | — | 7.10 | 6.50 |

*Original water content 3.5%
Calculated: 3.1% water = monohydrate, 6.1% water = dihydrate As can be seen by the results described above in Table 3, the crystalline cefepime dihydrochloride monohydrate remained essentially unchanged after 14 days of exposure to an environment of 55% relative humidity (RH). However, when the same crystalline monohydrate form is exposed to environments having 87% RH and 80% RH at 37° C., the monohydrate readily picked up a second mole of water within 2 hours to form the labile cefepime dihydrochloride dihydrate as characterized by the X-ray powder diffraction pattern shown in FIG. 2 and by the FT-IR absorption spectrum shown in FIG. 4.

In addition, the short-term hydration and dehydration of cefepime dihydrochloride monohydrate was studied gravimetrically. Two hundred and fifty milligrams of cefepime dihydrochloride monohydrate (KF=3.5% water) was spread thinly on a large glass dish and then placed at 25° C./87% RH. To monitor hydration, the sample was reweighed periodically to determine the amount of water gain. After 20 hours at 25° C./87% RH, the solids were transferred to a 25° C./33% RH chamber and dehydration was followed by reweighing the sample at selected time intervals as in Table 4.

TABLE 4

Hydration/Dehydration of Cefepime Dihydrochloride Monohydrate

| Time (Hours) | Storage Conditions | % Water Content* |
| --- | --- | --- |
| 0. | 25° C./87% RH | 3.5 # |
| 0.25 | 25° C./87% RH | 5.9 |
| 0.50 | 25° C./87% RH | 6.5 |
| 0.75 | 25° C./87% RH | 7.1 |
| 1.00 | 25° C./87% RH | 7.1 |
| 1.25 | 25° C./87% RH | 6.8 |
| 1.50 | 25° C./87% RH | 6.3 |
| 1.75 | 25° C./87% RH | 6.4 |
| 2.00 | 25° C./87% RH | 6.3 |
| 20.00 | 25° C./87% RH | 6.3 |
| 0. | 25° C./33% RH | 6.3 |
| 1.00 | 25° C./33% RH | 4.1 |
| 2.00 | 25° C./33% RH | 3.7 |
| 3.00 | 25° C./33% RH | 3.2 |
| 4.00 | 25° C./33% RH | 3.3 |
| 5.00 | 25° C./33% RH | 3.7 |
| 6.00 | 25° C./33% RH | 3.3 |
| 24.00 | 25° C./33% RH | 3.6 |
| 32.00 | 25° C./33% RH | 3.6 |
| 144.00 | 25° C./33% RH | 3.3 |

*By gravimetric determination
By Karl Fischer titration
Calculated: 3.1% water = monohydrate, 6.1% = dihydrate The results of the hydration/dehydration experiments shown above in Table 4 clearly demonstrate that the crystalline forms of the monohydrate and the labile dihydrate of the prior art are dependent on the relative humidities of the environment.

In contrast, the crystalline cefepime dihydrochloride dihydrate of the present invention is stable when exposed to both very low (vacuum) and high humidity environments. Three different samples of crystalline dihydrate of the present invention were subjected to various drying conditions as described in Table 5. As can be seen by the levels of hydration as determined by various methods of analysis, the per cent of water content of each sample remained essentially constant within experimental error at about 6%. The results shown in Table 5 confirm that the two moles of water in the cefepime dihydrochloride dihydrate of the present invention are tightly bound in the needle-like crystals. Microscopy and X-ray diffraction patterns on other samples confirmed maintenance of crystalline integrity.

TABLE 5

Stable Cefepime Dihydrochloride Dihydrate Dehydration Experiments
Percent Water Content (Karl Fischer)

| Drying Conditions | Sample Number | | |
| --- | --- | --- | --- |
| | 0123-65B | 28676-82B | 29849-14B |
| Initial | 6.25 | 6.13 | |
| 24 hr 24° C. P$_2$O$_5$ Vacuum | | | 6.30 |
| 24 hr 50° C. P$_2$O$_5$ Vacuum | | 5.74 | 6.13 |
| 48 hr 50° C. P$_2$O$_5$ Vacuum | | 6.11 | |
| 24 hr 50° C. Oven | 5.86* | | |
| 24 hr 60° C. Oven | 6.11* | | |
| 24 hr 70° C. Oven | 5.78* | 6.21 | |
| 96 hr 30° C. Oven | | 6.31 | |
| 96 hr 40° C. Oven | | 6.08 | |
| 96 hr 50° C. Oven | | 6.14 | |
| 96 hr 60° C. Oven | | 6.12 | |
| 96 hr 70° C. Oven | | 6.21 | |

*Average of KF and TGA values
Average of 2 KF values
Calculated: Dihydrate = 6.1% water The hygroscopicity of the crystalline cefepime dihydrochloride dihydrate of the present invention was investigated by exposing 20 to 30 mg samples to humidity chambers of 25° C./55% RH, 25° C./87% RH or 37° C./80% RH in open, 10 mL Type I glass vials. At periodic time intervals the vials were removed, stoppered, sealed and tested by Karl Fischer titration. As shown below by the results in Table 6, both samples showed essentially no increases in water content after 4 weeks. Thus, no evidence of hygroscopicity was observed for the crystalline dihydrate of the present invention when stored at high humidity conditions.

TABLE 6

Hygroscopicity of Stable Cefepime Dihydrochloride Dihydrate Percent Water Content (Karl Fischer)

| Storage Conditions | Sample Number | |
|---|---|---|
| | 28676-82B | 29849-14B |
| Initial | 5.92 | 5.60 |
| 25° C./55% RH | | |
| 1 Day | 6.09 | 5.52 |
| 7 Day | 5.99 | |
| 14 Day | 5.68 | 5.96 |
| 28 Day | 5.45 | 6.07 |
| 25° C./87% RH | | |
| 1 Day | 5.99 | 6.02 |
| 7 Day | 5.96 | |
| 14 Day | 5.66 | 5.90 |
| 28 Day | 5.50 | 6.29 |
| 37° C./80% RH | | |
| 1 Day | 6.12 | 5.86 |
| 7 Day | 5.87 | |
| 14 Day | 5.51 | 5.54 |
| 28 Day | 5.42 | 6.32 |

Calculated: Dihydrate = 6.1% water

The desired broad-spectrum antibiotic cefepime dihydrochloride dihydrate which is substantially free of the anti-isomer and the $\Delta^2$ isomer may be prepared by the N-acylation of 7-amino-3-[(1-methyl-1pyrrolidinio)-methyl]-ceph-3-em-4-carboxylate hydriodide (Compound I) which is substantially free of the $\Delta^2$ isomer with the syn-isomer of 2-(2-aminothiazol-4-yl)-2-methoxyimino acetyl chloride hydrochloride (Compound II) which is substantially free of the anti-isomer. Compound I may be prepared by the general procedures described by S. P. Brundidge, et al. in U.S. Pat. No. 4,868,294, and Compound II may be prepared by the general procedure as described herein in Example 1.

According to the acylation process, the cephalosporin intermediate (Compound I) may advantageously be silylated in an inert organic solvent, and preferably, acetonitrile or dichloromethane to form an in situ solution of a soluble silylated derivative. However, it is important to add sufficient silylating agent and, if necessary, a base to solubilize the cephalosporin intermediate (Compound I) before the anhydrous solution is treated with Compound II, and advantageously, by the general procedures described in Examples 4 and 5. Silylating agents which may be used are well known to those skilled in the art. Preferably, trimethylchlorosilane or a mixture of trimethylchlorosilane and hexamethyldisilazane and, most preferably, a mixture of trimethylchlorosilane and hexamethyldisilazane may be used in the acylation process.

Although at least one molar equivalent of a silylating agent and at least one molar equivalent of a base are required in the reaction, it was found in practice that it was advantageous to use about two molar equivalents of a silylating agent and about two molar equivalents or less of a base to obtain a solution of the soluble silylated intermediate. However, when the silylating agent is a mixture of trimethylchlorosilane and hexamethyldisilazane, it is preferable not to add any base to the preparation of the soluble silylated derivative. As will be appreciated by those skilled in the art, hexamethyldisilazane, as a silylating agent, will produce a base by-product which is sufficient to neutralize some of the acid which is produced. Since excess base is deleterious to the production of the desired antibiotic which is substantially free of the $\Delta^2$ isomer, a mixture of trimethylchlorosilane and hexamethyldisilazane is most preferred in the present invention. The amount of $\Delta^3$ to $\Delta^2$ isomerization in the cephalosporin nucleus is sensitive to the reaction conditions employed in the preparation of the soluble silylated derivative and in the N-acylation thereof with the acid chloride hydrochloride (Compound II) to produce cefepime dihydrochloride hydrate. The amount of isomerization is dependent on factors such as the amount and order of addition of base, the solvent and the temperature employed in the process. Most importantly, basic conditions resulting from the use of excess base or from the addition of base prior to the addition of silylating agent or acid chloride hydrochloride (Compound II) will increase isomerization of the cephem double bond from $\Delta^3$ to $\Delta^2$. Therefore, it is most preferred to maintain non-basic reaction conditions during the anhydrous acylation.

The soluble silylated derivative which is generated in situ is then treated with the acid chloride hydrochloride (Compound II) and, preferably, with one molar equivalent and, most preferably, a slight excess of the acid chloride hydrochloride of (Compound II) followed by an equimolar amount and, preferably, less than an equimolar amount of a base relative to the amount of (Compound II) to produce a mixture containing the desired antibiotic. Preferably, the amount of acid chloride hydrochloride (Compound II) and the base is slowly added in portions. Although the addition of reactants may be carried out all at once if the temperature and non-basic conditions of the reaction can be controlled, it is advantageous to add the reactants in two or three portions to ensure complete reaction.

When the N-acylation of the soluble silylated derivative is complete as ascertained by known detection methods available in the art, for example, thin-layer chromatography, high pressure liquid chromatography and spectroscopic methods; then, according to the preferred process of the acylation, sufficient water is added to the reaction mixture to dissolve, if desired, visible solids and produce a diphasic solution of organic phase and water. The amount of water to be added to the reaction mixture is determined by the selection and quantity of the inert organic solvent used in the process and should be sufficient to give or cause phase separation. Once phase separation has occurred, it is advantageous to separate and discard the organic phase to produce an aqueous rich solution containing the desired antibiotic.

The solution is then treated with a sufficient amount of hydrochloric acid and, optionally, with a water-miscible organic solvent to induce the crystallization of the preferred crystalline cefepime dihydrochloride hydrate. Most preferably, the aqueous rich solution obtained from the anhydrous acylation is treated with a sufficient amount of hydrochloric acid to induce and ensure crystallization of said antibiotic, cefepime dihydrochloride hydrate when a water-miscible organic solvent such as acetone is added. The amount of water-miscible organic solvent to be added should be sufficient to produce complete crystallization of said antibiotic and, advantageously, in an amount of about 2 to about 9 volumes of the aqueous phase to produce the temperature stable crystalline cefepime dihydrochloride monohydrate or dihydrate which is substantially free of the anti-isomer and the $\Delta^2$ isomer.

When it is desired to prepare only the cefepime dihydrochloride monohydrate, the rich aqueous solution from the anhydrous acylation is advantageously treated with a sufficient amount of hydrochloric acid and diluted with an appropriate amount of a water-miscible organic solvent as described herein to ensure the crystallization of the desired monohydrate form. Alternatively, when it is desired to prepare the stable cefepime dihydrochloride dihydrate, the rich aqueous solution is advantageously treated with a greater equivalent concentration of hydrochloric acid and an amount of water-miscible organic solvent to hold the crystallization at the cloud point before additional organic solvent is added to complete the crystallization. However, it should be appreciated by those skilled in the art that if the isolation step from the aqueous rich solution of the process is not carefully controlled, it is possible that a mixture of crystalline cefepime dihydrochloride monohydrate and dihydrate forms may be produced. In any event, the preparation of only one of the desired hydrates can be prepared from either hydrate or a mixture of hydrates by following the recrystallization procedures described herein.

Alternatively, the broad-spectrum antibiotic cefepime dihydrochloride dihydrate which is substantially free of the anti-isomer and the $\Delta^2$ isomer can be prepared by the aqueous-organic N-acylation of Compound I with the syn-isomer of the acid chloride hydrochloride (Compound II) as described in Example 3.

Suitable solvents which may be used in the aqueous acylation process are aqueous-organic solvents such as water with water-miscible organic solvents such as methanol, ethanol, isopropanol, butanol, acetone, tetrahydrofuran, acetonitrile, dioxane, dimethylacetamide, dimethylformamide or the like, and preferably, aqueous-acetone. The pH of the process is controlled by titrating with a suitable inorganic or organic base, and preferably, with ammonium hydroxide, triethylamine, N-methylmorpholine or the like.

The acylation is advantageously carried out at a pH of about 5 to about 7.5 and, preferably, at a pH of about 6.2 to 6.8. The process may be carried out at a temperature of about $-50°$ C. to about room temperature and, preferably, at about $-10°$ C. to $-40°$ C. After the acylation is completed, the reaction mixture is acidified with an appropriate acid and, preferably, with a sufficient amount of hydrochloric acid to induce and ensure crystallization of said antibiotic, cefepime dihydrochloride hydrate when a water-miscible organic solvent such as acetone is added. The amount of water-miscible organic solvent to be added should be sufficient to produce complete crystallization of said antibiotic and, advantageously, in an amount of about 2 to about 9 volumes of the aqueous amount of the aqueous-organic reaction mixture to produce the temperature stable crystalline cefepime dihydrochloride monohydrate or dihydrate which is substantially free of the anti-isomer and the $\Delta^2$ isomer.

The crystalline cefepime dihydrochloride monohydrate prepared by the present acylation processes may be used to prepare a stable crystalline cefepime dihydrochloride dihydrate by recrystallization under controlled concentrations of solvent and hydrochloric acid, and the amount of time held at the cloud point (initial crystallization) as described herein. Alternatively, the crystalline cefepime dihydrochloride dihydrate of the present invention may be prepared by the anhydrous or aqueous acylation process as described herein.

The utility of cefepime is shown in Abruaki et al, U.S. Pat. No. 4,406,899. The stable dihydrate form of cefepime dihydrochloride produced by the present process or produced by the conversion via recrystallization of the monohydrate exhibits the antibiotic properties of the above-mentioned cefepime of U.S. Pat. No. 4,406,899 and finds utility as an antibiotic in like manner.

When the present inventors prepared physical admixtures of the crystalline stable cefepime dihydrochloride dihydrate and L(+) arginine under typical manufacturing procedures such as described in Method A of Example 8, it was found that the admixture exhibited poor solid state stability at elevated temperatures of 40° C. to 50° C. As can be seen by the results in Table 7, the admixture lost 10.4% and 36.3% of cefepime activity after 3 months at 40° C. and 50° C., respectively, as ascertained by reverse phase HPLC using a $\mu$-Bondapak C-18 column and a mobile phase of 5-7% acetonitrile and 0.015M pentane sulfonic acid, sodium salt, pH 4 at a flow rate of 2 mL per minute.

However, the present inventors have found that physical admixtures of stable cefepime dihydrochloride dihydrate and L(+) arginine which are vacuum-dried under a variety of conditions including the use of a lyophilizer as a source of heat and vacuum, as exemplified in Table 8, a marked improvement in solid state stability was observed as compared to the physical admixture in Table 7 which had lost about 9.1% of cefepime activity after storage at 50° C. for 2 weeks. Consequently, the present inventors prepared physical admixtures of crystalline stable cefepime dihydrochloride dihydrate and L(+) arginine, and vacuum-dried the vials in a lyophilizer at 40° C. for 3 days. As can be seen by the long term stability data shown in Table 9, the physical admixture was found to exhibit solid state stability at elevated temperatures of 40° C. and 50° C. and confirmed the need to remove free extraneous water from the physical admixtures of the present invention.

TABLE 7

Solid State Stability of Stable Cefepime Dihydrochloride Dihydrate/L(+) Arginine Admixture*

| Storage Conditions | | | |
|---|---|---|---|
| Temp. | Time (months) | Cefepime % Remaining | Water Content % (KF)** |
| Initial | | 100.0 | 3.97 |
| 30° C. | 1 | 96.9 | 4.01 |
|  | 2 | 94.9 | 4.53 |
|  | 3 | 94.6 | 4.23 |
|  | 6 | 93.4 | 4.24 |
| 40° C. | 14 days | 98.7 | 3.77 |
|  | 1 | 93.7 | 4.36 |
|  | 2 | 91.9 | 4.87 |
|  | 3 | 89.6 | 4.66 |
|  | 6 | 83.4 | 4.30 |
| 50° C. | 14 days | 90.9 | 3.81 |
|  | 1 | 80.9 | 4.01 |
|  | 2 | 71.6 | 4.70 |
|  | 3 | 63.7 | 4.53 |

*Sealed vials filled with the physical admixture were prepared using typical manufacturing operations with a relative humidity generally less than about 35% (Method A).
**Water content by Karl Fischer was carried out using typical procedures without any additional precautions.

TABLE 8

Solid State Stability of Stable Cefepime
Dihydrochloride Dihydrate/L(+) Arginine Admixture
After Storage at 50° C. for 2 Weeks*

| Sample | Drying Conditions** | Cefepime % Remaining | Water Content % (KF)*** |
|---|---|---|---|
| A | Vacuum dry over $P_2O_5$ at 24° C. for 3 days | 99.6 | — |
| B | Vacuum dry over $P_2O_5$ at 50° C. for 3 days | 98.8 | — |
| C | Lyophilizer-freeze at −40° C. for 3 hrs. dry at 25° C. for 102 hrs. | 99.1 | 4.0 |
| D | Vacuum dry over $P_2O_5$ at 24° C. for 1 day | 97.2 | 4.05 |
| E | Vacuum dry over $P_2O_5$ at 50° C. for 1 day | 97.6 | 4.4 |
| F | Vacuum dry in Lyophilizer at 25° C. for 3 days | 98.9 | 2.3 |
| G | Vacuum dry at 40° C. for 2 days | 99.7 | 2.4 |
| H | Vacuum dry in Lyophilizer at 30° C. for 2 days | 98.8 | 3.7 |
| I | Vacuum dry at 50° C. for 1 day | 99.0 | 4.5 |

*Vials filled with the physical admixture were dried under various conditions as listed and then sealed for the stability studies.
**Vacuum was generated using a desiccator attached to a high vacuum pump.
***Karl Fischer values were obtained after drying and before vials were placed in the 50° C. stability station. Initial values before drying were 4.76% and 4.74%.

TABLE 9

Solid State Stability of Stable Cefepime
Dihydrochloride Dihydrate/L(+) Arginine Admixture*

| Storage Conditions | | | |
|---|---|---|---|
| Temp. | Time (months) | Cefepime % Remaining | Water Content % (KF)** |
| Initial | | 100.0 | 1.97 |
| 30° C. | 1 | 100.5 | 0.76 |
| | 3 | 99.8 | 0.32 |
| 40° C. | 1 | 100.2 | 0.88 |
| | 2 | 100.3 | 1.66 |
| | 3 | 99.1 | 0.35 |
| 50° C. | 1 | 98.8 | 2.63 |
| | 2 | 98.8 | 2.28 |
| | 3 | 97.8 | 0.31 |

*Vials filled with the physical admixture were vacuum-dried in a lyophilizer at a vacuum of about 100 mTorr for 3 days at 40° C. and then sealed (Method B).
**Water content by Karl Fischer was carried out using preweighed sealed samples. The variability of the data is a result of various time exposures of the sample to the atmosphere.

Furthermore, it should be appreciated by those skilled in the art that anhydrous L(+) arginine is extremely hygroscopic (strong desiccant) and it can accept two moles of water of crystallization and yet continue to maintain its crystalline integrity, even in highly humid environments. Alternatively, the two moles of water are quite labile and can be easily removed, as for example at 24° C. to 40° C. under vacuum.

Physical admixtures of crystalline stable cefepime dihydrochloride dihydrate (500 mg of cefepime active) and L(+) arginine dihydrate (690 mg of L(+) arginine) were prepared as generally described in Method A of Example 8 and having an initial water content of 9.21% KF. This blend was filled into vials and then stored at various temperatures. After storage for 2 weeks, the blend was found to be unstable with extensive degradation of the active cefepime ingredient as analyzed by the HPLC method described herein. For example, after storage for 2 weeks at 40° C. and 50° C. HPLC analysis showed that 87.6% and 22.9%, respectively, of the cefepime ingredient remained. However, when 3 vials of the same lot were vacuum-dried at 24° C. for 6 hours followed by 48 hours at 40° C. using a desiccator attached to a high vacuum pump, the vacuum-dried blend which had a water content of 3.8% KF showed 99.6% of cefepime remaining (HPLC analysis) after 2 weeks of storage at 50° C. The results of the above experiments additionally demonstrate and confirm the solid state stability of the vacuum-dried physical admixture of the present invention.

The stable crystalline cefepime dihydrochloride dihydrate described herein is formed into an injectable composition by diluting with sterile water and buffering to a pH of 3.5–7 to form an injectable concentration of 1 mg/ml up to 400 mg/ml of zwitterion. Suitable buffering agents include, for example, trisodium orthophosphate, sodium bicarbonate, sodium citrate, N-methylglucamine and L(+) arginine. For intramuscular or intravenous administration to an adult human, a total dosage of from about 750 to about 6000 mg per day in divided doses is normally sufficient.

The stable crystalline cefepime dihydrochloride dihydrate described herein is not desirably formed into an injectable composition simply by the addition of sterile water because the stable crystalline cefepime dihydrochloride dihydrate when dissolved provides very low pH compositions (1.8–2.5) which provide painful sensation on injection. As indicated above, it has been found that this shortcoming is overcome by forming the stable crystalline cefepime dihydrochloride dihydrate into a physical, i.e. solid, admixture with pharmaceutically acceptable, normally solid non-toxic organic or inorganic bases in proportions to provide a pH ranging from about 3.5 to about 7, preferably from about 4 to about 6, on dilution of the vacuum-dried admixture with water to injectable concentration of 1 mg/ml up to 400 mg/ml of zwitterion, e.g. zwitterion activity of 250 mg/ml as determined by HPLC assay.

The exact proportions of ingredients in the physical admixture vary from lot to lot of the antibiotic since the purity of the antibiotic varies from lot to lot. The proportions of ingredients are established for a particular lot by pre-titrating in respect to a sample to obtain a selected pH within the aforementioned range.

The physical admixture is prepared by blending the stable crystalline cefepime dihydrochloride dihydrate and the base into a uniform blend, e.g. utilizing a standard V-blender in a dry atmosphere. The blend is then vacuum-dried on trays before being filled into a vial or other container, or preferably, the blend is filled into a vial and then vacuum-dried such as described in Example 8.

The bases for use in the admixture include, for example, trisodium orthophosphate, sodium bicarbonate, sodium citrate, N-methylglucamine and L(+) arginine. L(+) Arginine is most preferred since the admixture is reconstituted to provide an injectable composition which on injection would provide less pain in animals. L(+) Arginine is advantageously utilized in a proportion to provide a pH of 3.5–6 on dilution of the admixture with water to provide a composition with a zwitterion activity of 250 mg/ml (as determined by HPLC assay).

The stable cefepime dihydrochloride dihydrate antibiotic described herein and substantially vacuum-dried physical admixtures containing the antibiotic can be stored without refrigeration or insulated packaging and still retain high potency.

DESCRIPTION OF SPECIFIC EMBODIMENTS

Example 1

Syn 2-(2-aminothiazol-4-yl)-2-methoxyimino acetyl chloride hydrochloride

Syn 2-(2-aminothiazol-4-yl)-2-methoxyimino acetic acid (84.7 g, 421 mmol) in dichloromethane (570 ml) was milled under nitrogen for 20 minutes in a blender. The resulting fine suspension was diluted with dichloromethane (100 ml), and transferred under nitrogen to a 1 L Buchi jacketed reactor. The reactor was pressurized with nitrogen (5 psi) and the mixture stirred at 375 rpm and cooled to −2° C. Hydrogen chloride (15.3 g, 421 mmol) was introduced into the headspace of the reactor at 0.2 g per minute. There was a temperature rise of 2° C. The mixture was stirred for a further 30 minutes at 0° C. milled for 3 minutes in the blender, then cooled to −35° C. and transferred under nitrogen over 5 minutes to a well stirred slurry of Vilsmeier reagent, also at −35° C. The slurry of Vilsmeier reagent was prepared by adding oxalyl chloride (56.1 g, 439 mmol) portionwise to a solution of dimethylformamide (33.8 g, 462 mmol) in dichloromethane (880 ml) at 0° C., followed by cooling to −35° C. During the addition, the reaction temperature rose to −28° C. After the addition, the reaction mixture was seeded with product. After a further 2.5 hours at −28° C. to −35° C. the mixture was filtered and the filter cake washed with dichloromethane (350 ml) under nitrogen. Nitrogen was passed through the cake for 30 minutes, then the solid was dried in vacuo at room temperature for 12 hours. The title compound was obtained as an off-white powder (95.2 g, 89% uncorrected yield).

Anal. Calcd. for $C_6H_7N_3O_2SCl_2$: C, 28.14; H, 2.76; N, 16.41; S, 12.52; Cl, 27.68; Found: C, 28.11; H, 2.62; N, 16.20; S, 12.22; Cl, 26.74.

$^1$H NMR (CD$_3$OD) δ: 4.06 (s, 3H, CH$_3$), 7.12 (s, 1H, C-5H). Signals were also seen at 7.18 (s, C-5H) corresponding to ca. 4% of acid hydrochloride salt, and at 7.80 (s, C-5H) corresponding to ca. 2% of the anti-isomer. After derivatization with diethylamine in acetonitrile, HPLC analysis showed the title compound (as its diethylamide derivative) with a retention time of 9.6 minutes, the starting acid with a retention time of 2.8 minutes, and the anti-isomer (as its diethylamide derivative) with a retention time of 16.4 minutes. The ratio of syn-isomer:starting acid:anti-isomer was 90:4:2.

EXAMPLE 2

Preparation of 7-[2-(2-aminothiazol-4-yl)-2-(Z)-methoxyiminoacetamido]-3-[(1-methyl-1-pyrrolidinio)-methyl]ceph-3-em-4-carboxylate dihydrochloride hydrates To a cold (−22° C.) solution of acetone (120 ml) and water (40 ml), 7-amino-3-[(1-methyl-1-pyrrolidinio)-methyl]ceph-3-em-4-carboxylate hydriodide (14.67 g active; 0.0345 mol) and syn-2-(2-aminothiazol-4-yl)-2-methoxyimino acetyl chloride hydrochloride (9.93 g active; 0.0388 mol) were added simultaneously and separately as solids over 25 minutes. The reaction pH was maintained between 5.0 and 7.0 using a Radiometer ABU80 autotitrator filled with triethylamine set at a pH 6.5 endpoint, and the temperature was maintained between −20° C. and −30° C. Once the reactant addition was finished, the resulting opaque slurry was warmed to 0°–5° C. and stirred until the solids dissolved at which point high performance liquid chromatography indicated the acylation was complete. The reaction mixture was polish filtered, and the filtrate was divided into two equal portions.

Method A

One portion of the above filtrate was acidified with 12N hydrochloric acid (8.8 ml; 0.106 mol) and diluted with acetone (114 ml) until the filtrate clouded. The filtrate was seeded with stable cefepime dihydrochloride dihydrate crystals (0.5 g) and the slurry was heated at 40° C. for approximately 3 hours. The mixture was cooled at 0°–5° C. for 1 hour and filtered. The product was washed with acetone and dried in vacuo at room temperature. The dihydrochloride salt of the title compound was crystallized with 93.3% purity (7.34 g; 67.3% stoichiometric weight yield). Water content by Karl Fischer analysis was 4.1% and FT-IR (Diffuse Reflectance with KBr) analysis with absorbance peaks at 3574 cm$^{-1}$ and 3432 cm$^{-1}$ indicated the product to be a mixture of monohydrate (granular-like crystals) and dihydrate (needle-like crystals) forms of the title compound.

Method B

The second filtrate portion was acidified with 12N hydrochloric acid (8.8 ml; 0.106 mol) and diluted with acetone (206 ml) over 1 hour. The slurry was held until crystallization was observed, then it was cooled to 0°–5° C. and held 1 hour. The slurry was filtered and the product was washed with acetone then dried in vacuo at 45° C. The dihydrochloride salt of the title compound was crystallized with 95.3% purity (8.6 g; 85.3% stoichiometric weight yield). Water content by Karl Fischer analysis was 4.6% and FT-IR (Diffuse Reflectance with KBr) analysis indicated that the product was the monohydrate form of the title compound with less than about 0.4% of the dihydrate form.

EXAMPLE 3

Preparation of 7-[2-(2-aminothiazol-4-yl)-2-(Z)-methoxyiminoacetamido]-3-[(1-methyl-1-pyrrolidinio)-methyl]ceph-3-em-4-carboxylate dihydrochloride dihydrate To a cold (−22° C.) solution of acetone (120 ml) and water (40 ml), 7-amino-3-[(1-methyl-1-pyrrolidinio)-methyl]ceph-3-em-4-carboxylate hydriodide (14.61 g active; 0.0344 mol) and syn 2-(2-aminothiazol-4-yl)-2-methoxyimino acetyl chloride hydrochloride (9.94 g active; 0.0388 mol) were added simultaneously and separately as solids over 25 minutes. The reaction pH was maintained between 5.0 and 7.5 using a Radiometer ABU80 autotitrator filled with triethylamine set at a pH 6.5 endpoint, and the temperature was maintained between −20° C. and −30° C. Once the reactant addition was finished, the resulting opaque slurry was warmed to 0°–5° C. and stirred until the solids dissolved at which point high performance liquid chromatography indicated the acylation was complete. The reaction mixture was polish filtered, and the filtrate was divided into two equal portions.

Method A

One portion of the above filtrate was acidified with 12N hydrochloric acid (11.7 ml; 0.1404 mol) and acetone was added to the filtrate with stirring until it clouded. The filtrate was seeded with stable cefepime dihydrochloride dihydrate crystals (0.3 g) and the slurry was heated at 50° C. for approximately 1 hour.

The mixture was cooled to room temperature, diluted with acetone and stirred for 15 hours. The slurry was again heated at 40° C. for 1 hour and diluted with acetone. A total of 280 ml of acetone was used to crystallize the product. After cooling the mixture gradually to 0°–5° C. for 1 hour, the slurry was filtered, washed with acetone (125 ml) and the product dried in vacuo at 45° C. The title compound, cefepime dihydrochloride dihydrate, was isolated with a 97.8% purity (8.19 g; 80.9% stoichiometric weight yield). Water content by Karl Fischer analysis was 6.5%, and FT-IR (Diffuse Reflectance with KBr) analysis showed absorbance peaks at 3574 cm$^{-1}$ and 3432 cm$^{-1}$ which confirmed the product to be the dihydrate (needle-like crystals) form.

Method B

The second filtrate portion was acidified with 12N hydrochloric acid (14.6 ml; 0.1752 mol) and acetone was added to the filtrate with stirring until it clouded. The filtrate was seeded with stable cefepime dihydrochloride dihydrate crystals (0.3 g) and the slurry was stirred for approximately 1.5 hours at room temperature. The mixture was diluted further with acetone, stirred at room temperature for 15 hours then heated at 40° C. for 1 hour. Additional acetone was added to dilute the mixture to provide a total of 231 ml of acetone. After cooling gradually to 0°–5° C. for 1 hour, the product was collected by filtration, washed with 125 ml of acetone and dried in vacuo at 45° C. The title compound, cefepime dihydrochloride dihydrate, was isolated with 96.3% purity (8.68 g; 85.7% stoichiometric weight yield). Water content by Karl Fischer analysis was 6.7%, and FT-IR (Diffuse Reflectance with KBr) analysis showed absorbance peaks at 3574 cm$^{-1}$ and 3432 cm$^{-1}$ which confirmed the product to be the dihydrate (needle-like crystals) form.

EXAMPLE 4

Anhydrous acylation of 7-amino-3-[(1-methyl-1-pyrrolidinio)methyl]ceph-3-em-4-carboxylate HI salt using 2-(2-aminothiazol-4-yl)-2-methoxyimino acetyl chloride hydrochloride (syn-isomer)

Under a nitrogen atmosphere, 7-amino-3-[(1-methyl-1-pyrrolidinio)methyl]ceph-3-em-4-carboxylate HI salt (50 g, 0.1176 mol) was cooled to −20° C. in 500 ml of acetonitrile. Trimethylchlorosilane (39 ml, 2.5 eq.) and triethylamine (38 ml, 2.3 eq.) were added, keeping the temperature at or below −10° C. After the silyl mixture was stirred for 1.5 hours at −10° C., 2-(2-aminothiazol-4-yl)-2-methoxyimino acetyl chloride hydrochloride (syn-isomer obtained from Example 1) was added in two aliquots (15 g, 0.50 eq each). Another 8 ml (0.5 eq.) of triethylamine was added with 7.5 g (0.25 eq.) of 2-(2-aminothiazol-4-yl)-2-methoxyimino acetyl chloride hydrochloride (syn-isomer). The slurry was stirred at −10° C. for 15 minutes, and then, 150 ml of water was added and stirred at ambient temperature to dissolve all solids. The acetonitrile layer was separated from the rich aqueous, and 6N HCl (2.5 eq.) was added to the aqueous with 400 ml of acetone. The solution was seeded and allowed to crystallize for 15 minutes. A further 1000 ml of acetone was added to complete crystallization. The slurry was stirred 1 hour and then filtered, washed with 400 ml of acetone, and dried at about 40° C. Yield was 56.51 g (84.1% stoich. weight) of cefepime (98.6% pure by HPLC assay as cefepime.2HCl.H$_2$O), which is identical to the cefepime.2HCl.H$_2$O described by Kaplan, et al, in U.S. Pat. No. 4,910,301, issued Mar. 20, 1990.

EXAMPLE 5

Preparation of 7-[2,-(2-aminothiazol-4-yl)-2-(Z)-methoxyiminoacetamido]-3-[(1-methyl-1-pyrrolidinio)-methyl]ceph-3-em-4-carboxylate dihydrochloride hydrates Under an inert atmosphere at room temperature, 7-amino-3-[(1-methyl-1-pyrrolidinio)methyl ]ceph-3-em-4-carboxylate hydriodide (14.67 g; 0.0345 mol) was suspended in dichloromethane (150 ml). Trimethylchlorosilane (4.7 ml) and hexamethyldisilazane (7.7 ml) were added to the slurry and the mixture was warmed to 25°–30° C. over 1.5 hours. The reaction was then cooled to about −50° C., and syn 2-(2-aminothiazol-4-yl) -2-methoxyimino acetyl chloride hydrochloride (7.24 g; 0.0283 mol) was added in three portions over 35 minutes while the temperature gradually rose to −30° C. Triethylamine (1.47 ml) and 1.78 g (0.0069 mol) of syn 2 -(2-aminothiazol-4-yl)-2 -methoxyimino acetyl chloride hydrochloride were added and the acylation continued between −20° C. and −25° C. for approximately 1 hour. Once the reaction was complete (as indicated by HPLC), the mixture was warmed to −5° C. and then 56 ml of water and 10 ml of dimethylacetamide were added. The reaction slurry was stirred at 25° C. until the solids dissolved. The phases were separated and the aqueous phase was polish filtered. The aqueous phase was decolorized with activated carbon (3 g), filtered and the filtrate was divided into two equal portions.

Method A

One portion of the rich aqueous filtrate was acidified with 12N hydrochloric acid (11.7 ml; 0.14 mol). The slurry was seeded with stable cefepime dihydrochloride dihydrate (0.5 g) and the slurry was heated at 40° C. for 1 hour then held at room temperature overnight. The mixture was diluted further with acetone (126 ml), stirred at room temperature for 0.5 hour, then cooled at 0°–5° C. for 1 hour. The product was collected by filtration, washed with acetone and dried in vacuo at 45° C. The dihydrochloride dihydrate form of the title compound (needle-like crystals) was obtained with a 96.3% purity (9.11 g; 87.6% stoichimetric weight yield). Water content by Karl Fischer analysis was 6.3% and FT-IR (Diffuse Reflectance with KBr) analysis showed absorbance peaks at 3574 cm$^{-1}$ and 3432 cm$^{-1}$.

Method B

The second portion of rich aqueous filtrate was acidified with 6N hydrochloric acid (15 ml; 0.09 mol), diluted with acetone (280 ml) over 20 minutes then cooled at 0°–5° C. for 1 hour. The slurry was filtered, washed with acetone and dried in vacuo at 45° C. The dihydrochloride monohydrate form (granular-like crystals) of the title compound was obtained with 95.5% purity (8.38 g; 83.1% stoichiometric wt. yield). Water content by Karl Fischer analysis was 3.9%.

EXAMPLE 6

Preparation of Stable Cefepime Dihydrochloride Dihydrate

Stable cefepime dihydrochloride dihydrate crystals were typically prepared by dissolving cefepime dihydrochloride monohydrate at approximately 100 mg/mL in water containing about 2–4 mole equivalents of HCl yielding crystalline cefepime dihydrochloride dihydrate. Five to ten volumes of acetone (about 24° C.) were added with stirring over 0.5 to 1 hour. After 1–2 additional hours of stirring, the crystals were collected by vacuum filtration, washed with acetone and vacuum-dried at 40°–50° C. for 24–48 hours. Various analyses (e.g. Karl Fischer water titration, microscopy, NMR, FT-IR, DSC, TGA, X-ray powder diffraction) verified the product to be the stable cefepime dihydrochloride dihydrate which was comparable to the stable dihydrochloride dihydrate form of cefepime prepared by other procedures described herein.

EXAMPLE 7

Conversion of Cefepime Dihydrochloride Monohydrate to Stable Cefepime Dihydrochloride Dihydrate Cefepime dihydrochloride monohydrate (300 g, purity by HPLC 99.9%, KF 3.8%) was dissolved in deionized water (1200 ml). Hydrochloric acid 6N (132 ml, 1.5 equivalent) was added. The solution was filtered and washed with deionized water (300 ml).

Acetone (1500 ml) was added to the filtered solution. Additional acetone (4000 ml) was added dropwise over 20 minutes. The solution was held at cloud point until heavy dihydrate crystals formed (needles by microscopic analysis; seeding optional at cloud point). Additional acetone (8000 ml) was added over a 25 minute period. The thick slurry was stirred at 25° C. for one hour.

The crystal form was confirmed to be the stable dihydrate (needles) by microscopic analysis comparing the crystals to an authentic sample. The slurry was filtered and washed with acetone (2×1500 ml). The cake was dried at 40° C. in vacuo for 15 hours. The yield of crystalline stable cefepime dihydrochloride dihydrate was 305.10 g (98.6%), purity by HPLC 99.0% and KF 6.5%.

EXAMPLE 8

Preparation of Stable Cefepime Dihydrochloride Dihydrate/L(+) Arginine Admixtures Stable cefepime dihydrochloride dihydrate, 150 grams, and L(+) arginine, 86.25 g, were weighed and placed in a V-blender. The mixture was blended for 32 minutes. The blend was then screened through a 40 mesh US standard sieve, returned to the blender and blended for another 32 minutes.

Method A

The blend was then filled into 15 cc Type I flint glass vials (0.966 g of the blend per vial which gives 0.5 g of cefepime activity per vial). The vials were stoppered with West 1816 stoppers, sealed and stored at various stability stations. The relative humidity during a typical manufacturing operation was generally less than 35%.

Method B

The blend was then filled into 15 cc Type I flint glass vials. The vials were subjected to vacuum drying by one of the methods described herein such as in Tables 8 and 9, for example, vacuum drying with or without a desiccant at 24° C. to 50° C. for about 1–3 days, vacuum drying in a lyophlizer at 25° C. to 50° C. for about 1–3 days, vacuum drying in a lyophlizer-freeze at −40° C. for 3 hours and dried at 25° C. for about 4 days or the like. The vials are then stoppered with West 1816 stoppers, sealed and stored at various stability stations. The relative humidity during a typical blend manufacturing operation was generally less than 35%.

Method C

The blend is vacuum-dried on trays by one of the methods described herein such as in Tables 8 and 9, for example, vacuum drying with or without a desiccant at 24° C. to 50° C. for about 1–3 days, vacuum drying in a lyophlizer at 25° C. to 50° C. for about 1–3 days, vacuum drying in a lyophlizer-freeze at −40° C. for 3 hours and dried at 25° C. for about 4 days or the like. The blend is then filled into 15 cc Type I flint glass vials (0.966 g of the blend per vial which gives 0.5 g of cefepime activity per vial). The vials were stoppered with West 1816 stoppers, sealed and stored at various stability stations. The relative humidity during a typical manufacturing operation was generally less than 35%.

We claim:

1. A temperature and moisture stable crystalline dihydrochloride dihydrate salt of 7-[α-(2-aminothiazol-4-yl)-α-(Z)-methoxyiminoacetamido]-3-[(1-methyl-1-pyrrolidinio)methyl]-3-cephem-4-carboxylate in a vacuum-dried physical admixture with a pharmaceutically acceptable non-toxic organic or inorganic base selected from the group consisting of sodium salts with weak non-toxic anions, N-methylglucamine and L(+) arginine in proportions to provide a pH of about 3.5 to about 7 on dilution of the admixture with water to injectable concentration.

2. A vacuum-dried physical admixture as recited in claim 1 wherein the salt is the temperature and moisture stable crystalline 7-[α-(2-aminothiazol-4-yl)-α-(Z)-methoxyiminoacetamido]-3-[(1-methyl-1pyrrolidinio)-methyl]-3-cephem-4-carboxylate dihydrochloride dihydrate having the following x-ray powder diffraction pattern wherein d represents the interplanar spacing and $I/I_o$ represents the relative percent intensity:

| d | $I/I_o$ (%) |
|---|---|
| 13.14 | 15 |
| 12.78 | 13 |
| 8.82 | 24 |
| 6.62 | 18 |
| 6.41 | 100 |
| 4.94 | 17 |
| 4.79 | 10 |
| 4.74 | 12 |
| 4.52 | 13 |
| 4.41 | 36 |
| 4.1 | 63 |
| 3.75 | 50 |
| 3.6 | 11 |
| 3.53 | 16 |
| 3.41 | 36 |
| 3.31 | 9 |
| 3.19 | 22 |
| 2.84 | 30 |
| 2.67 | 16 |
| 2.62 | 6 |
| 2.57 | 14 |
| 2.5 | 4 |
| 2.48 | 9 |
| 2.27 | 15 |

3. A vacuum-dried physical admixture as recited in claim 1 or 2 wherein the pharmaceutically acceptable non-toxic organic base is L(+) arginine.

* * * * *

UNITED STATES PATENT AND TRADEMARK OFFICE
CERTIFICATE OF CORRECTION

PATENT NO. : 5,401,842
DATED : March 28, 1995
INVENTOR(S) : Nassar, et al.

It is certified that error appears in the above-indentified patent and that said Letters Patent is hereby corrected as shown below:

On the title page, please insert the reference to the application being disclaimed.

Notice: The portion of the term of this patent subsequent to February 21, 2112 has been disclaimed.

On front cover page, please correct assignee to read:

Assignee: --Bristol-Myers Squibb Company--

Signed and Sealed this

Twenty-sixth Day of December, 1995

Attest:

BRUCE LEHMAN

*Attesting Officer*  *Commissioner of Patents and Trademarks*